United States Patent
Ni et al.

(10) Patent No.: US 10,815,162 B2
(45) Date of Patent: Oct. 27, 2020

(54) METHOD FOR DIRECTLY PREPARING AROMATICS FROM SYNGAS

(71) Applicant: DALIAN INSTITUTE OF CHEMICAL PHYSICS, CHINESE ACADEMY OF SCIENCES, Dalian, Liaoning Province (CN)

(72) Inventors: Youming Ni, Dalian (CN); Wenliang Zhu, Dalian (CN); Zhongmin Liu, Dalian (CN); Yong Liu, Dalian (CN); Zhiyang Chen, Dalian (CN); Hongchao Liu, Dalian (CN); Xiangang Ma, Dalian (CN); Shiping Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 16/763,026

(22) PCT Filed: Oct. 29, 2018

(86) PCT No.: PCT/CN2018/112424
§ 371 (c)(1),
(2) Date: May 11, 2020

(87) PCT Pub. No.: WO2019/095986
PCT Pub. Date: May 23, 2019

(65) Prior Publication Data
US 2020/0270187 A1   Aug. 27, 2020

(30) Foreign Application Priority Data
Nov. 15, 2017 (CN) .......................... 2017 1 1133394

(51) Int. Cl.
*C07C 1/04* (2006.01)
*B01J 35/02* (2006.01)
(Continued)

(52) U.S. Cl.
CPC ............... *C07C 1/043* (2013.01); *B01J 21/18* (2013.01); *B01J 29/405* (2013.01); *B01J 29/46* (2013.01);
(Continued)

(58) Field of Classification Search
CPC . C07C 1/043; C07C 2529/46; C07C 2529/48; B01J 35/023; B01J 37/04;
(Continued)

(56) References Cited

U.S. PATENT DOCUMENTS

2014/0018232 A1   1/2014 Wang et al.

FOREIGN PATENT DOCUMENTS

CN    101270297 A    9/2008
CN    101422743 A    5/2009
(Continued)

OTHER PUBLICATIONS

International Search Report dated Jan. 30, 2019 in corresponding International application No. PCT/CN2018/112424; 4 pages.

*Primary Examiner* — Jafar F Parsa
(74) *Attorney, Agent, or Firm* — Maier & Maier, PLLC (57) ABSTRACT

A method for preparing aromatics from syngas, which includes a) contacting a raw material stream containing syngas with a catalyst in a reaction zone under reaction conditions sufficient to convert at least part of the raw material to obtain a reaction effluent; b) separating the reaction effluent to obtain at least a recycle stream containing gas-phase hydrocarbons having 1 to 4 carbon atoms and unconverted syngas and a liquid stream containing hydrocarbons having 5 or more carbon atoms; c) returning the
(Continued)

recycle stream to the reaction zone; and d) separating aromatic products from the liquid stream, wherein the catalyst includes at least one of an inert carrier-confined highly dispersed metal oxide material, an acidic molecular sieve, and, optionally, graphite powder and a dispersant.

12 Claims, 3 Drawing Sheets

(51) Int. Cl.
  *B01J 37/04* (2006.01)
  *B01J 37/08* (2006.01)
  *B01J 37/03* (2006.01)
  *B01J 37/00* (2006.01)
  *B01J 37/06* (2006.01)
  *B01J 37/02* (2006.01)
  *B01J 29/40* (2006.01)
  *B01J 29/48* (2006.01)
  *B01J 29/46* (2006.01)
  *B01J 21/18* (2006.01)

(52) U.S. Cl.
  CPC ............. *B01J 29/48* (2013.01); *B01J 35/023* (2013.01); *B01J 35/026* (2013.01); *B01J 37/0009* (2013.01); *B01J 37/0236* (2013.01); *B01J 37/031* (2013.01); *B01J 37/036* (2013.01); *B01J 37/04* (2013.01); *B01J 37/06* (2013.01); *B01J 37/088* (2013.01); *C07C 2529/46* (2013.01); *C07C 2529/48* (2013.01)

(58) Field of Classification Search
  CPC ...... B01J 37/088; B01J 37/031; B01J 37/036; B01J 37/0009; B01J 37/06; B01J 37/0236; B01J 29/405; B01J 29/48; B01J 29/46; B01J 21/18; B01J 35/026
  See application file for complete search history.

(56) References Cited

FOREIGN PATENT DOCUMENTS

| | | | |
|---|---|---|---|
| CN | 102895990 | A | 1/2013 |
| CN | 103372456 | A | 10/2013 |
| CN | 105944751 | A | 9/2016 |
| CN | 106215972 | A | 12/2016 |
| CN | 106268924 | A | 1/2017 |
| CN | 106423195 | A | 2/2017 |
| CN | 106540740 | A | 3/2017 |

METHOD FOR DIRECTLY PREPARING AROMATICS FROM SYNGAS

FIELD

The present invention relates to a method for directly preparing aromatics from syngas.

BACKGROUND

Aromatics (especially Benzene, Toluene and Xylene, which are collectively called BTX) are important basic organic chemical raw materials. At present, aromatics are mainly produced using petroleum as a raw material, and its production technologies include, for example, catalytic reforming of naphtha, gasoline hydrogenation, aromatics extraction, conversion of heavy aromatics to light aromatics, and aromatization of light hydrocarbons. However, due to the depletion of petroleum resources, it is of great significance to develop other production routes such as coal chemical routes to produce aromatics. For example, the technology of producing aromatics (MTA) using methanol as a raw material for coal chemical products has been extensively studied, and some technologies have been commercialized.

The process of directly preparing aromatics from syngas omits the intermediate step of producing methanol and/or dimethyl ether, and is therefore very attractive.

Chinese patent application CN 105944751A teaches a catalyst for directly preparing aromatics from syngas. The catalyst is composed of a metal active component, an auxiliary agent and a hydrogen-type ZSM-5 molecular sieve material. The metal active component is one or more oxides of iron, molybdenum, cobalt, zinc and gallium, and the auxiliary agent is one or more oxides of sodium, potassium, calcium, magnesium, vanadium, chromium, manganese and copper.

Chinese patent applications CN 101422743 A, CN 106215972 A, CN 106540740A and CN 106268924A also disclose catalysts suitable for the direct preparation of aromatics from syngas.

There is still a need for a method suitable for directly preparing aromatics from syngas and a catalyst used therein, which has high aromatic hydrocarbon yield and selectivity.

SUMMARY

In order to overcome the problems in the prior art, the inventors conducted diligent research. As a result, it was found that a catalyst containing at least one of an inert carrier-confined highly dispersed metal oxide material, an acidic molecular sieve, and optionally graphite powder and a dispersant is very suitable for a method for directly preparing aromatics from syngas. The method of directly preparing aromatics from syngas using the catalyst can achieve a high conversion rate of raw materials and a high yield and high selectivity of product aromatics. The present invention has been completed based on the above findings.

Therefore, an object of the present invention is to provide a method for directly preparing aromatics from syngas, which comprises:

a) contacting a raw material stream containing syngas with a catalyst in a reaction zone under reaction conditions sufficient to convert at least part of the raw material to obtain a reaction effluent;

b) separating the reaction effluent to obtain at least a recycle stream containing gas-phase hydrocarbons having 1 to 4 carbon atoms and unconverted syngas and a liquid stream containing hydrocarbons having 5 or more carbon atoms;

c) returning the recycle stream to the reaction zone; and d) separating aromatic products from the liquid stream, wherein the catalyst comprises at least one of an inert carrier-confined highly dispersed metal oxide material, an acidic molecular sieve, and optionally graphite powder and a dispersant, wherein in the inert carrier-confined highly dispersed metal oxide material, the inert carrier is at least one of silicon oxide and aluminum oxide, and the content of the metal oxide in terms of metal is less than or equal to 10% by mass, based on the weight of the inert carrier-confined highly dispersed metal oxide material; and the acidic molecular sieve is selected from modified acidic ZSM-5 molecular sieve, modified acidic ZSM-11 molecular sieve and mixtures thereof. In one embodiment, the reaction zone comprises a fixed bed reactor, or a plurality of fixed bed reactors in series and/or parallel.

In one embodiment, the reaction conditions comprise: a reaction temperature of ranging from 300° C. to 450° C., a reaction pressure of ranging from 0.5 MPa to 10.0 MPa, a molar ratio of hydrogen to carbon monoxide in the syngas of ranging from 1:9 of 9:1, and the volume hourly space velocity of syngas under the standard state of ranging from 1000 $h^{-1}$ to 20000 $h^{-1}$.

In a first aspect, the present invention provides a method for directly preparing aromatics from syngas, the method comprises:

a) contacting a raw material stream containing syngas with a catalyst in a reaction zone under reaction conditions sufficient to convert at least part of the raw material to obtain a reaction effluent;

b) separating the reaction effluent to obtain at least a recycle stream containing gas—phase hydrocarbons having 1 to 4 carbon atoms and unconverted syngas and a liquid stream containing hydrocarbons having 5 or more carbon atoms;

c) returning the recycle stream to the reaction zone; and d) separating aromatic products from the liquid stream, wherein the catalyst comprises at least one of an inert carrier-confined highly dispersed metal oxide material, an acidic molecular sieve, and optionally graphite powder and a dispersant, wherein in the inert carrier-confined highly dispersed metal oxide material, the inert carrier is at least one of silicon oxide and aluminum oxide, and the content of the metal oxide in terms of metal is less than or equal to 10% by mass, based on the weight of the inert carrier-confined highly dispersed metal oxide material; and the acidic molecular sieve is selected from modified acidic ZSM-5 molecular sieve, modified acidic ZSM-11 molecular sieve and mixtures thereof.

Catalyst for Directly Preparing Aromatics from Syngas

As described above, the catalyst used in the method of the present invention comprises at least one of an inert carrier-confined highly dispersed metal oxide material, an acidic molecular sieve, and optionally graphite powder and a dispersant, wherein in the inert carrier-confined highly dispersed metal oxide material, the inert carrier is at least one of silicon oxide and aluminum oxide, and the content of the metal oxide in terms of metal is less than or equal to 10% by mass, based on the weight of the inert carrier-confined highly dispersed metal oxide material; and the acidic molecular sieve is selected from modified acidic ZSM-5 molecular sieve, modified acidic ZSM-11 molecular sieve and mixtures thereof.

In one embodiment, the metal oxide in the inert carrier-confined highly dispersed metal oxide material is an oxide of at least one of metals except aluminum and radioactive elements. Preferably, the metal oxide in the inert carrier-confined highly dispersed metal oxide material is an oxide of at least one of zinc, chromium, zirconium, copper, manganese, platinum and palladium. More preferably, the metal oxide in the inert carrier-confined highly dispersed metal oxide material is an oxide of at least one of zinc, chromium and zirconium.

In one embodiment, the content of the metal oxide in the inert carrier-confined highly dispersed metal oxide material in terms of metal is less than or equal to 10% by weight; preferably less than or equal to 5% by weight; more preferably less than or equal to 2% by weight, based on the weight of the inert carrier-confined highly dispersed metal oxide material. Unless otherwise specified, the term "metal oxide content" as used herein does not include the content of alumina, if alumina is present.

In one embodiment, the average particle size of the metal oxide in the inertcontrol-confined highly dispersed metal oxide material is less than or equal to 100 nm, preferably less than or equal to 50 nm, and more preferably less than or equal to 20 nm.

In a preferred embodiment, the X-ray powder diffraction pattern of the inertcontrol-confined highly dispersed metal oxide material does not show the characteristic diffraction peak of the metal oxide.

The inertcontrol-confined highly dispersed metal oxide material is different from the conventional metal composite oxide materials known in the art. For example, the former has high metal oxide dispersion (no characteristic metal oxide XRD diffraction peak), small metal oxide mass fraction (generally less than 10%) and small metal oxide average particle size (generally less than 100 nm), and usually has a large specific surface area (generally greater than 400 m$^2$/g). Conventional composite metal oxide materials, such as copper-zinc-aluminum composite oxide materials (CuZnAlOx) for low-temperature methanol synthesis, zinc-chromium-aluminum composite oxide materials (Zn-CrAlOx) for high-temperature methanol synthesis and zinc-zirconium composite oxide materials (ZnZrOx) known in the art, have a metal oxide mass fraction generally greater than 80%, have significant XRD diffraction peaks characteristic of metal oxides, and have a specific surface area generally less than 100 m$^2$/g.

Without wishing to be limited to any particular theory, it is believed that the inert carrier present in a large amount in the inertcontrol-confined highly dispersed metal oxide material of the present invention can not only provide a large specific surface area but also function stably as a methyl oxide of catalyzing active components due to the confinement effect.

In one embodiment, the average particle diameter of the inertcontrol-confined highly dispersed metal oxide material is less than or equal to 5 mm, preferably less than or equal to 1 mm, more preferably less than or equal to 0.5 mm, still more preferably less than or equal to 0.1 mm, still more preferably less than or equal to 0.05 mm.

In some embodiments, the inertcontrol-confined highly dispersed metal oxide material can be prepared by a coprecipitation-calcination method. For example, in the case of using alumina as a carrier, the inertcontrol-confined highly dispersed metal oxide material may be prepared as follows: a salt of catalyzing active metal and an aluminum salt are formulated into an aqueous solution of mixed metal salt; the aqueous solution of mixed metal salt is contacted with an aqueous solution of precipitant to coprecipitate the metal ions in the aqueous solution of mixed metal salt; aged; and the precipitate is washed, dried and calcined. Examples of the precipitant include but are not limited to sodium carbonate, potassium carbonate, ammonium carbonate, sodium bicarbonate, potassium bicarbonate, ammonium bicarbonate, ammonia water, sodium hydroxide, potassium hydroxide and mixtures thereof.

In one embodiment, the temperature during the coprecipitation is in a range from 0° C. to 90° C., the pH value during the coprecipitation is in a range from 7.0 to 8.5, the aging time is not less than 1 h, and the calcination temperature is in a range from 300° C. to 700° C.

In one specific embodiment, the inertcontrol-confined highly dispersed metal oxide material is prepared as follows: the aluminum salt and the salt of catalyzing active metal are formulated into a aqueous solution of mixed metal salt with a total metal ion concentration of ranging from 0.1 mol/L to 3.5 mol/L; then the aqueous solution of mixed metal salt is contacted with an aqueous solution of precipitant with a molar concentration of ranging from 0.1 mol/L to 3.5 mol/L at a temperature of ranging from 0° C. to 90° C. under stirring to coprecipitate the metal ions in the metal salt, and then aged for a period of time, the pH value of the solution during the coprecipitation process can be in a range from 7.0 to 8.5, and the aging time is not less than 1 hour; the resulting precipitate is filtered and washed, and then calcined at a temperature of, for example, ranging from 300° C. to 700° C. to prepare an inertcontrol-confined highly dispersed metal oxide material.

There is no particular limitation on the kinds of the aluminum salt and the salt of catalyzing active metal, as long as they are water-soluble, for example, having a water solubility of more than 1 g/L at 25° C. Examples of the aluminum salt and the salt of catalyzing active metal include but are not limited to hydrochloride, sulfate and nitrate.

There is no particular limitation on the contacting method of the aqueous solution of mixed metal salt and the aqueous solution of precipitant. In one specific embodiment, the contacting can be accomplished by parallel feeding, forward feeding or reverse feeding.

In other embodiments, the inertcontrol-confined highly dispersed metal oxide material can be prepared by a sol-gel method. For example, in the case where at least silica is used as a carrier, the inertcontrol-confined highly dispersed metal oxide material can be prepared as follows: an aqueous solution of a salt of catalyzing active metal and an aqueous solution of a precipitant are added to the siloxy group compound, the coprecipitation and sol-gel reaction are allowed to proceed, and then the obtained gel is washed, dried and then calcined to prepare the inertcontrol-confined highly dispersed metal oxide material. Examples of the precipitant include but are not limited to one or more of ammonium carbonate, ammonia water, ammonium bicarbonate, ammonium dihydrogen carbonate and urea.

In one embodiment, the siloxy group compound is an alkyl orthosilicate, and examples thereof include but are not limited to methyl orthosilicate, ethyl orthosilicate, n-propyl orthosilicate, isopropyl orthosilicate, n-butyl orthosilicate, isobutyl orthosilicate, t-butyl orthosilicate and mixtures thereof.

The acidic molecular sieve component in the catalyst of the present invention is selected from modified acidic ZSM-5 molecular sieve, modified acidic ZSM-11 molecular sieve and mixtures thereof.

In some embodiments, the modification of the acidic molecular sieve is one or more of phosphorus modification, boron modification, silicon modification, alkaline earth metal modification and rare earth metal modification.

In some embodiments, the atomic ratio of silicon to aluminum in the acidic ZSM-5 and ZSM-11 molecular sieves is Si/Al=3 to 200, preferably Si/Al=100 to 150.

In some embodiments, the crystals of the acidic ZSM-5 and ZSM-11 molecular sieves are on the micrometer scale or nanometer scale, and the crystals contain a microporous structure or a mesoporous-microporous structure. The modified acidic molecular sieve is commercially available or can be prepared by a method known per se. There is no particular limitation on the specific method for preparing the modified acidic molecular sieve. For example, the modified acidic molecular sieve can be obtained by modifying the commercially available acidic ZSM-5 molecular sieve or acidic ZSM-11 molecular sieve.

In one specific embodiment, the acidic molecular sieve can be impregnated with, for example, $H_3PO_4$, $NH_4H_2PO_4$, or $(NH_4)_2HPO_4$ aqueous solutions, and then the impregnated acidic molecular sieve is dried and then calcined to obtain a phosphorus—modified acidic molecular sieve containing ranging from 0.5% to 10.0% by weight of phosphorous based on the weight of the modified molecular sieve.

In another specific embodiment, the acidic molecular sieve can be impregnated with, for example, the aqueous solution of $H_3BO_3$, and then the impregnated acidic molecular sieve is dried and then calcined to obtain a boron-modified acidic molecular sieve containing 0.5% to 10.0% by weight of boron based on the weight of the modified molecular sieve.

In yet another specific embodiment, a silicon-modified acidic molecular sieve can be prepared by treatment with a siloxane compound in a liquid-phase deposition method and/or treatment with a silane compound in a vapor-phase deposition method. The siloxane compounds and silane compounds that can be used are represented by the following structural formulas:

wherein $R_1$, $R_2$, $R_3$, $R_4$, $R_5$, $R_6$, $R_7$ and $R_8$ are each independently $C_{1-10}$ alkyl. An example of the siloxane compound is ethyl orthosilicate, and an example of the silane compound is tetramethylsilane.

In one specific embodiment, the liquid-phase deposition method is performed as follows: the silicone compound is dissolved in an inert organic solvent to provide a silicone compound solution, and then the acidic molecular sieve is soaked or impregnated with the solution, dried and then calcined to obtain a silicon-modified acidic molecular sieve. Based on the weight of the modified molecular sieve, the silicon loading in the silicon—modified acidic molecular sieve may be in a range from 0.5% to 10.0% by weight, and the silicon loading does not include the original silicon in the acidic molecular sieve. The inert organic solvent may be any solvent that does not react with the siloxane compound and molecular sieve, such as n-hexane, cyclohexane and n-heptane.

In one specific embodiment, the vapor-phase deposition method is performed as follows: the silane compound gas is passed through an acidic molecular sieve, and then the treated acidic molecular sieve is calcined to obtain a silicon—modified acidic molecular sieve. Based on the weight of the modified molecular sieve, the silicon loading in the silicon—modified acidic molecular sieve may be in a range from 0.5% to 10.0% by weight, and the silicon loading does not include the original silicon in the acidic molecular sieve.

In one specific embodiment, the acidic molecular sieve can be impregnated with an aqueous solution of an alkaline earth salt or rare earth metal salt, and then the impregnated acidic molecular sieve can be filtered, dried and calcined to obtain an alkaline earth metal or rare earth metal—modified acidic molecular sieve containing ranging from 0.5% to 10.0% by weight of alkaline earth metal or rare earth metal based on the weight of the modified molecular sieve.

In one embodiment, the average particle size of the acidic molecular sieve is less than or equal to 5 mm, preferably less than or equal to 0.5 mm, more preferably less than or equal to 0.1 mm, still more preferably less than or equal to 0.05 mm.

In some embodiments, the dispersant is selected from alumina, silica and mixtures thereof. There are no particular restrictions on alumina, silica or alumina-silica that can be used as a dispersant, and they are commercially available from many suppliers.

There is no particular limitation on the graphite powder that can be used in the present invention, and they are commercially available from many suppliers. In some embodiments, the graphite powder has an average particle size of ranging from 0.05 to 5 microns.

In one embodiment, the catalyst used in the method of the present invention can be prepared by a method comprising the following steps:

(1) providing an inert carrier-confined highly dispersed metal oxide material;

(2) providing a modified acidic molecular sieve;

(3) mixing at least one of the inertcontrol-confined highly dispersed metal oxide material obtained in step (1), the modified acidic molecular sieve obtained in step (2) and optional graphite powder and dispersant, and molding the resulting mixture.

In some embodiments, the catalyst of the present invention comprises ranging from 10% to 90% by weight of the inertcontrol-confined highly dispersed metal oxide material. The lower limit of the content of the inertcontrol-confined highly dispersed metal oxide material may be 12%, 15%, 18%, 20%, 22%, 25%, 28%, 30%, 32%, 35%, 38%, 40%, 42%, 45%, 48% or 50% by weight, and the upper limit may be 88%, 85%, 82%, 80%, 78%, 75%, 72%, 70%, 68%, 65%, 62%, 60%, 58%, 55%, 52% or 50% by weight, based on the weight of the catalyst.

In some embodiments, the catalyst of the present invention comprises ranging from 10% to 90% by weight of the acidic molecular sieve. The lower limit of the content of the acidic molecular sieve may be 12%, 15%, 18%, 20%, 22%, 25%, 28%, 30%, 32%, 35%, 38%, 40%, 42%, 45%, 48% or 50% by weight, and the upper limit may be 88%, 85%, 82%, 80%, 78%, 75%, 72%, 70%, 68%, 65%, 62%, 60%, 58%, 55%, 52% or 50% by weight, based on the weight of the catalyst.

In some embodiments, the catalyst of the present invention comprises ranging from 0% to 10% by weight, such as ranging from 0% to 8% by weight, ranging from 0% to 7% by weight, ranging from 0% to 6% by weight, or ranging from 0% to 5% by weight of the graphite powder, based on the weight of the catalyst.

In some embodiments, the catalyst of the present invention comprises ranging from 0% to 40% by weight, such as ranging from 0% to 38% by weight, ranging from 0% to 35% by weight, ranging from 0% to 30% by weight, or ranging from 0% to 25% by weight of the dispersant, based on the weight of the catalyst.

In some embodiments, the catalyst of the present invention comprises ranging from 10% to 90% by weight of the inertcontrol-confined highly dispersed metal oxide material, ranging from 10% to 90% by weight of the acidic molecular sieve, ranging from 0% to 10% by weight of the graphite powder, and ranging from 0% to 40% by weight of the dispersant, wherein the total content of the inertcontrol-confined highly dispersed metal oxide material and the acidic molecular sieve is in a range from 60% to 100% by weight, and the weight percentage is based on the total weight of the catalyst. In some preferred embodiments, the catalyst of the present invention comprises ranging from 20% to 80% by weight of the inertcontrol-confined highly dispersed metal oxide material, ranging from 20% to 80% by weight of the acidic molecular sieve, ranging from 0% to 5% by weight of the graphite powder, and ranging from 0% to 30% by weight of the dispersant, the weight percentage is based on the total weight of the catalyst.

There is no particular limitation on the shape of the catalyst, only that it is suitable for the intended application process. In one specific embodiment, the particle shape of the catalyst may be spherical, bar-shaped, cylindrical, semi-cylindrical, prismatic, clover-shaped, ring-shaped, pellet-shaped, regular or irregular particle-shaped or plate-shaped.

In the present invention, the terms "powder", "particle" and "powdered particle" are used interchangeably.

Method for Directly Preparing Aromatics from Syngas

As previously mentioned, in the process of the present invention, the raw material stream containing syngas is connected with the catalyst in the reaction zone under reaction conditions sufficient to convert at least part of the raw material to obtain a reaction effluent.

It is believed that the reactions taking place in the reaction zone are very complex and include a series of reaction processes, such as:

1) the reaction of directly preparing aromatics from syngas, for example:

2) alkylation of olefins with aromatics, for example:

Oxygen atom in CO mainly enters $CO_2$, so little waste water is produced during the reaction.

In the method of the present invention, syngas is used as a raw material. As used herein, the term "syngas" refers to a mixture of hydrogen and carbon monoxide. In the syngas raw material, the molar ratio of hydrogen to carbon monoxide may be in a range from 1:9 to 9:1, preferably ranging from 1:9 to 1:1.

In the method of the present invention, the reaction zone may be one or more fixed bed reactors. The fixed bed reactor can be operated in continuous mode. When using a plurality of fixed bed reactors, the plurality of reactors may be configured in series, parallel or a combination of series and parallel.

In the method of the present invention, the reaction conditions comprise: a reaction temperature of ranging from 300° C. to 450° C., a reaction pressure of ranging from 0.5 MPa to 10.0 MPa, a molar ratio of hydrogen to carbon monoxide in the syngas of ranging from 1:9 to 9:1, and the volume hourly space velocity of syngas under the standard state of ranging from 1000 $h^{-1}$ to 20000 $h^{-1}$.

In a preferred embodiment, the reaction conditions comprise: a reaction temperature of ranging from 320° C. to 400° C., a molar ratio of hydrogen to carbon monoxide in the syngas of ranging from 1:9 to 1:1, a reaction pressure of ranging from 5.0 MPa to 10.0 MPa, and the volume hourly space velocity of syngas under the standard state of ranging from 1000 $h^{-1}$ to 5000 $h^{-1}$.

In the method of the present invention, the reaction effluent produced in the contacting step may include aromatics, gas—phase hydrocarbons having 1 to 4 carbon atoms, and unconverted raw materials.

In one embodiment, the gas—phase hydrocarbons having 1 to 4 carbon atoms are at least one selected from methane, ethane, ethylene, propane, cyclopropane, propylene, n-butane, isobutane, cyclobutane, 1-butene, 2-butene, isobutene and butadiene.

In one embodiment, the aromatics are at least one selected from monocyclic aromatics containing 6 to 11 carbon atoms. Examples of the monocyclic aromatics containing 6 to 11 carbon atoms include but are not limited to benzene, toluene, ethylbenzene, p-xylene, m-xylene, o-xylene, mesitylene and mesitylene.

Separation of Reaction Effluent

In the method of the present invention, the reaction effluent is separated to obtain at least a recycle stream containing gas—phase hydrocarbons having 1 to 4 carbon atoms and unconverted syngas and a liquid stream containing hydrocarbons having 5 or more carbon atoms. This can be achieved by methods known per se such as gas-liquid separation. The liquid stream can then be sent to a subsequent separation device for further separation to obtain aromatic products, and the recycle stream can be sent to the reaction zone as part of the raw material stream.

The beneficial effects that the present applicant brought out include:

1) The method of the present invention uses a catalyst comprising at least one of the inertcontrol-confined highly dispersed metal oxide material, the acidic molecular sieve, and optionally graphite powder and the dispersant to directly convert syngas to aromatics, especially BTX.

2) The catalyst used in the method of the present invention has stable performance and long service life, and the performance of the catalyst does not decrease significantly after repeated regeneration.

3) Compared with the method known in the prior art for preparing aromatics from syngas via methanol and/or dimethyl ether, the method of the present invention reduces energy consumption.

4) The yield and selectivity of the aromatic product obtained by the method of the present invention are both high.

5) Compared with conventional metal composite oxide materials, the inertcontrol-confined highly dispersed metal oxide material used in the method of the present invention has a large specific surface, high catalytic activity, relatively low content of relatively expensive active metal oxide components, less heavy metal ion emission in the preparation process and easier to form into industrial catalyst.

DETAILED DESCRIPTION

The present invention will be described in detail below with reference to the examples, but the present invention is not limited to these examples.

Unless otherwise specified, the raw materials in the examples of the present invention are purchased through commercial channels.

In the examples, two Agilent 7890 gas chromatographs with a gas autosampler, a TCD detector connected to a TDX-1 packed column, and a FID detector connected to a FFAP and PLOT-Q capillary column are used for automatic gas composition analysis.

In the examples, conversion and selectivity are calculated based on carbon moles:

For the case of single-pass conversion of syngas and no material recycling:

> Conversion rate of carbon monoxide=[(number of moles of carbon monoxide in the feed)−(number of moles of carbon monoxide in the discharge)]÷(number of moles of carbon monoxide in the feed)×100%.

> Selectivity of aromatics=(number of moles of aromatics in the discharge)÷(number of moles of all hydrocarbon products in the discharge)× 100%.

Figure 1:
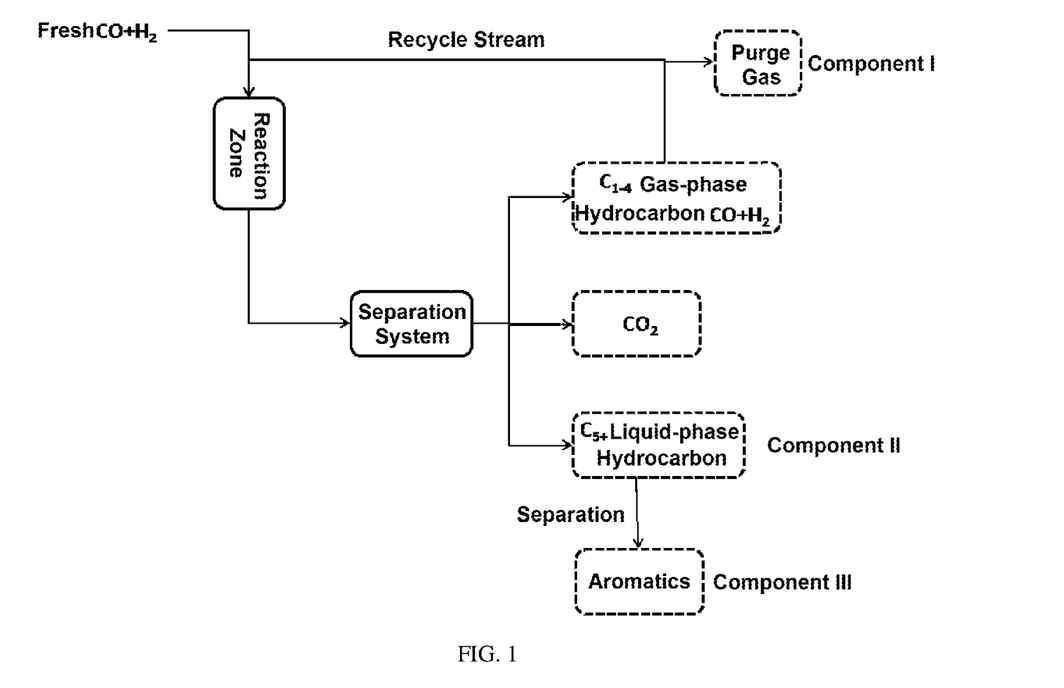
FIG. 1 is a schematic diagram of the $C_{1-4}$ gas-phase hydrocarbon circulation process in Examples 19-24 of the present application.

For the return of $C_{1-4}$ gas-phase hydrocarbon products to the reaction zone (see FIG. 1):

> Selectivity of aromatics=number of moles of aromatics in Component III÷(sum of number of moles of all hydrocarbons in Component I and Component II)×100%.

The return of $C_{1-4}$ gas-phase hydrocarbon products to the reaction zone has little effect on the conversion rate of CO.

Inert Carrier-Confined Highly Dispersed Metal Oxide Material

Example 1

Figure 2:
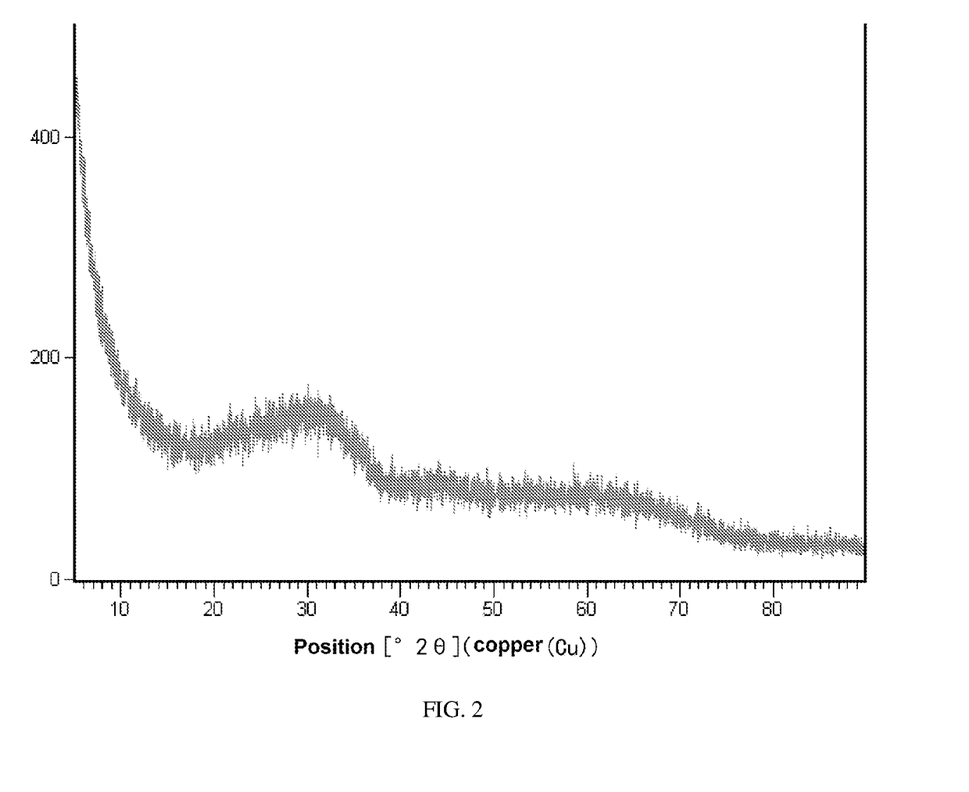
FIG. 2 is an XRD diagram of material A in Example 1 of the present application.

1 L of a mixed nitrate aqueous solution containing 0.05 mol/L $Zn^{2+}$ and 1.0 mol/L $Al^{3+}$ was prepared, a 0.5 mol/L ammonia solution was slowly added to it. The temperature of the coprecipitation reaction was controlled to 70° C. and the pH was 7.2 to coprecipitate the metal ions, and aged at this temperature for 4 h, filtered, washed and dried, and calcined at 500° C. for 4 h to obtain the alumina inertcontrol-confined highly dispersed zinc oxide material, which was designated as A. The mass fraction of zinc in A was 8.3%, and the XRD diagram was shown in FIG. 2.

Example 2

1 L of a mixed nitrate aqueous solution containing 0.02 mol/L $Zn^{2+}$, 0.02 mol/L $Cr^{3+}$ and 1.0 mol/L $Al^{3+}$ was prepared, a 1.0 mol/L ammonium carbonate solution was slowly added to it. The temperature of the coprecipitation reaction was controlled to 70° C. and the pH was 7.5 to coprecipitate the metal ions, and aged at this temperature for 4 h, filtered, washed and dried, and calcined at 500° C. for 4 h to obtain the alumina inertcontrol-confined highly dispersed zinc-chromium oxide material, which was designated as B. The mass fraction of zinc in B was 3.1%, and the mass fraction of chromium in B was 2.5%.

Example 3

1 L of a mixed nitrate aqueous solution containing 0.01 mol/L $Zn^{2+}$, 0.01 mol/L $Zr^{4+}$ and 1.0 mol/L $Al^{3+}$ was prepared, a 1.2 mol/L sodium carbonate solution was slowly added to it. The temperature of the coprecipitation reaction was controlled to 70° C. and the pH was 7.3 to coprecipitate the metal ions, and aged at this temperature for 4 h, filtered, washed and dried, and calcined at 500° C. for 4 h to obtain the alumina inertcontrol-confined highly dispersed zinc-zirconium oxide material, which was designated as C. The mass fraction of zinc in C was 1.5%, and the mass fraction of zirconium in C was 2.1%.

Example 4

1 L of a mixed nitrate aqueous solution containing 0.01 mol/L $Zn^{2+}$, 0.02 mol/L $Cu^{2+}$ and 1.0 mol/L $Al^{3+}$ was prepared, a 1.5 mol/L potassium carbonate solution was slowly added to it. The temperature of the coprecipitation reaction was controlled to 70° C. and the pH was 7.9 to coprecipitate the metal ions, and aged at this temperature for 4 h, filtered, washed and dried, and calcined at 500° C. for 4 h to obtain the alumina inertcontrol-confined highly dispersed zinc-copper oxide material, which was designated as D. The mass fraction of zinc in D was 1.5%, and the mass fraction of copper in D was 3.1%.

Example 5

100 mL of a mixed nitrate aqueous solution containing 0.2 mol/L $Zn^{2+}$ and 0.2 mol/L $Cr^{3+}$ was prepared. 100 mL of 1.0 mol/L urea aqueous solution was prepared. The above two solutions were added dropwise to 1 mol of tetraethyl orthosilicate, reacted at room temperature for 24 h, obtained a gel, dried at 100° C., and calcined at 500° C. for 4 h to obtain the silicon oxide inertcontrol-confined highly dispersed zinc-chromium oxide material, which was designated as E. The mass fraction of zinc in E was 1.8%, and the mass fraction of chromium in E was 1.5%.

Example 6

100 mL of a mixed nitrate aqueous solution containing 0.2 mol/L $Zn^{2+}$ and 0.2 mol/L $Zr^{4+}$ was prepared. 100 mL of 1.0 mol/L urea aqueous solution was prepared. The above two solutions were added dropwise to 1 mol of tetraethyl orthosilicate, reacted at room temperature for 24 h, obtained a gel, dried at 100° C., and calcined at 500° C. for 4 h to obtain the silicon oxide inertcontrol-confined highly dispersed zinc-chromium oxide material, which was designated as F. The mass fraction of zinc in F was 1.8%, and the mass fraction of zirconium in F was 2.5%.

Comparative Example 1

Figure 3:
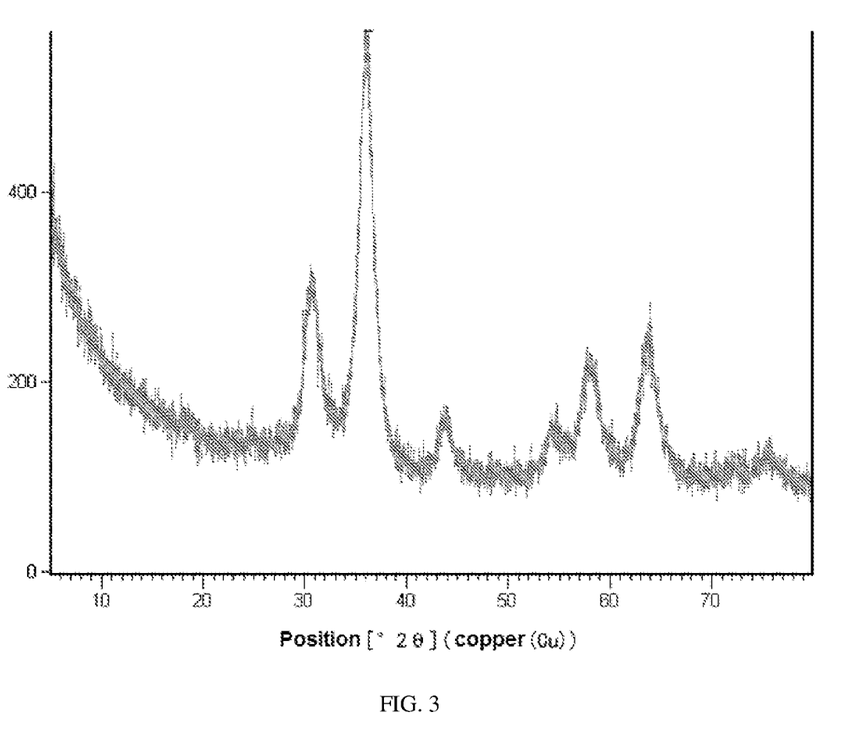
FIG. 3 is an XRD diagram of the material REF-1 in Comparative Example 1 of the present application.

1 L of a mixed nitrate aqueous solution containing 1.0 mol/L $Zn^{2+}$, 0.50 mol/L $Cr^{3+}$ and 0.20 mol/L $Al^{3+}$ was prepared, a 1.0 mol/L ammonium carbonate solution was slowly added to it. The temperature of the coprecipitation reaction was controlled to 70° C. and the pH was 7.5 to coprecipitate the metal ions, and aged at this temperature for 4 h, filtered, washed and dried, and calcined at 500° C. for 4 h to obtain the zinc-chromium composite oxide, which was designated as REF-1. The XRD diagram of REF-1 was shown in FIG. 3.

Preparation Of Modified Acidic Molecular Sieve

Example 7

The sodium-type ZSM-5 (Nankai University Catalyst Plant) with Si/Al=25 (atomic ratio) was exchanged with 0.8 mol/L ammonium nitrate aqueous solution three times at 80° C. to obtain the ammonium-type ZSM-5 molecular sieve, calcined at 550° C. for 4 h in air atmosphere, then immersed in $(NH_4)_2HPO_4$ aqueous solution at room temperature for 24 h at equal volume. After drying, it was calcined at 550° C. for 4 h in air atmosphere to obtain an acidic ZSM-5 molecular sieve with a P mass fraction of 4%, which was designated as G.

Example 8

The sodium-type ZSM-5 (Nankai University Catalyst Plant) with Si/Al=200 (atomic ratio) was exchanged with 0.8 mol/L ammonium nitrate aqueous solution three times at 80° C. to obtain the ammonium-type ZSM-5 molecular sieve, calcined at 550° C. for 4 h in air atmosphere, then immersed in $H_3BO_3$ aqueous solution at room temperature for 24 h at equal volume. After drying, it was calcined at 550° C. for 4 h in air atmosphere to obtain an acidic ZSM-5 molecular sieve with a B mass fraction of 8%, which was designated as H.

Example 9

The sodium-type ZSM-11 (Aoke Co., Ltd.) with Si/Al=40 (atomic ratio) was exchanged with 0.8 mol/L ammonium nitrate aqueous solution three times at 80° C. to obtain the ammonium-type ZSM-11 molecular sieve, calcined at 550° C. for 4 h in air atmosphere, then immersed in $H_3BO_3$ aqueous solution at room temperature for 24 h at equal volume. After drying, it was calcined at 550° C. for 4 h in air atmosphere to obtain an acidic ZSM-11 molecular sieve with a B mass fraction of 8%, which was designated as I.

Example 10

The sodium-type ZSM-5 (Aoke Co., Ltd.) with Si/Al=3 (atomic ratio) was exchanged with 0.8 mol/L ammonium nitrate aqueous solution three times at 80° C. to obtain the ammonium-type ZSM-5 molecular sieve, calcined at 550° C. for 4 h in air atmosphere, a solution of tetraethyl orthosilicate in cyclohexane was used to react at 50° C. for 4 h. After evaporation, it was calcined at 550° C. for 4 h in air atmosphere to obtain an acidic ZSM-5 molecular sieve with a Si mass fraction of 8% (excluding the original Si in the molecular sieve), which was designated as J.

Example 11

The sodium-type ZSM-5 (Fuxu Co., Ltd.) with Si/Al=80 (atomic ratio) was exchanged with 0.8 mol/L ammonium nitrate aqueous solution three times at 80° C. to obtain the ammonium-type ZSM-5 molecular sieve, calcined at 550° C. for 4 h in air atmosphere, nitrogen carried 5% by volume of tetramethylsilane was used, treated at 200° C. for 3 h, calcined at 550° C. for 4 h in air atmosphere to obtain an acidic ZSM-5 molecular sieve with a Si mass fraction of 2% (excluding the original Si in the molecular sieve), which was designated as K.

Example 12

The sodium-type ZSM-5 (Nankai University Catalyst Plant) with Si/Al=60 (atomic ratio) was exchanged with 0.8 mol/L ammonium nitrate aqueous solution three times at 80° C. to obtain the ammonium-type ZSM-5 molecular sieve, calcined at 550° C. for 4 h in air atmosphere, then immersed in mixed aqueous solution of magnesium nitrate and cerous nitrate at room temperature for 24 h at equal volume. After drying, it was calcined at 550° C. for 4 h in air atmosphere to obtain an acidic ZSM-5 molecular sieve with Mg and Ce mass fractions of 4% and 1% respectively, which was designated as L.

Mixed Catalyst Preparation

Example 13

The inertcontrol-confined highly dispersed metal oxide material A in Example 1 and the acidic molecular sieve G in Example 7 were uniformly mixed at a mass fraction of the inertcontrol-confined highly dispersed metal oxide material A of 75% and crushed into powder of less than 0.05 mm, and then compressed and sieved to make a 1-2 mm particle catalyst, which was designated as M. The preparation scheme was summarized in Table 1.

Examples 14-18

The preparation method was similar to Example 13, and the specific scheme was shown in Table 1.

Comparative Example 2

The metal composite oxide REF-1 in Comparative Example 1 and the acidic molecular sieve G in Example 7 were uniformly mixed at a mass fraction of the inertcontrol-confined highly dispersed metal oxide material A of 75% and crushed into powder of less than 0.05 mm, and then compressed and sieved to make a 1-2 mm particle catalyst, which was designated as REF-2.

TABLE 1

Preparation scheme of mixed catalyst

| Example | Catalyst No. | Inert Carrier-confined Highly Dispersed Metal Oxide Material No. | Mixed Acidic Molecular Sieve No. | Mass Fraction of Inert Carrier-confined Highly Dispersed Metal Oxide Material |
|---|---|---|---|---|
| 13 | M | A | G | 75% |
| 14 | N | B | H | 10% |
| 15 | O | C | I | 90% |
| 16 | P | D | J | 50% |
| 17 | Q | E | K | 80% |
| 18 | R | F | L | 65% |

Catalyst Performance Test

Example 19

500 g of the catalyst M was packed into a stainless steel reaction tube with an inner diameter of 28 mm, activated with 1000 ml/min hydrogen at 300° C. for 4 h, and reacted under the following conditions: reaction temperature (T)=400° C., reaction pressure (P)=4.0 MPa, the volumetric space velocity (GHSV) under standard conditions=6000 h$^{-1}$, and the volume fraction V(H$_2$)% of hydrogen in the syngas (mixed gas of CO and H$_2$)=40%. After the reaction was stabilized, the product was analyzed by gas chromatography to obtain the conversion rate of carbon monoxide and the selectivity of aromatics when C$_{1-4}$ gas-phase hydrocarbons were not recycled. The reaction results were shown in Table 2. Then, under the same reaction conditions, C$_{1-4}$ gas-phase hydrocarbons were returned to the reaction zone (as shown in FIG. 1). After the reaction was stabilized, when C$_{1-4}$ gas-phase hydrocarbons were recycled, the selectivity of aromatics was obtained. The reaction results were also shown in Table 2.

TABLE 2

Catalytic reaction results in Examples 19-24 and Comparative Example 3

| Examples/ Comparative Example | Catalyst | Reaction Condition | Conversion Rate of Carbon Monoxide (%) | Selectivity of Aromatics When C$_{1-4}$ Gas-phase Hydrocarbons were not Recycled (%) | Selectivity of Aromatics When C$_{1-4}$ Gas-phase Hydrocarbons were Recycled (%) |
|---|---|---|---|---|---|
| Example 19 | M | T = 400° C.; P = 4.0 MPa; GHSV = 6000 h$^{-1}$; V(H$_2$) % = 40% | 20.3 | 56.0 | 97.1 |
| Example 20 | N | T = 370° C.; P = 0.0 MPa; GHSV = 20000 h$^{-1}$; V(H$_2$) % = 90% | 58.0 | 32.7 | 95.2 |
| Example 21 | O | T = 300° C.; P = 0.5 MPa; GHSV = 1000 h$^{-1}$; V(H$_2$) % = 10% | 17.3 | 68.7 | 94.8 |
| Example 22 | P | T = 450° C.; P = 3.0 MPa; GHSV = 8000 h$^{-1}$; V(H$_2$) % = 65% | 38.9 | 59.1 | 97.7 |
| Example 23 | Q | T = 390° C.; P = 5.0 MPa; GHSV = 7000 h$^{-1}$; V(H$_2$) % = 30% | 29.1 | 65.4 | 98.1 |
| Example 24 | R | T = 340° C.; P = 7.0 MPa; GHSV = 12000 h$^{-1}$; V(H$_2$) % = 75% | 28.0 | 47.1 | 96.3 |
| Example 3 | REF-2 | T = 400° C.; P = 4.0 MPa; GHSV = 6000 h$^{-1}$; V(H$_2$) % = 40% | 12.3 | 10.5 | 28.3 | were not recycled. The reaction results were shown in Table 2. Then, under the same reaction conditions, C$_{1-4}$ gas-phase hydrocarbons were returned to the reaction zone (as shown in FIG. 1). After the reaction was stabilized, when C$_{1-4}$ gas-phase hydrocarbons were recycled, the selectivity of aromatics was obtained. The reaction results were also shown in Table 2.

Examples 20-24

The reaction conditions and reaction results were shown in Table 1. Other operations were the same as in Example 19.

Comparative Example 3

500 g of the catalyst REF-2 was packed into a stainless steel reaction tube with an inner diameter of 28 mm, activated with 1000 ml/min hydrogen at 300° C. for 4 h, and reacted under the following conditions: reaction temperature (T)=400° C., reaction pressure (P)=4.0 MPa, the volumetric space velocity (GHSV) under standard conditions=6000 h$^{-1}$, and the volume fraction V(H$_2$)% of hydrogen in the syngas (mixed gas of CO and H$_2$)=40%. After the reaction was stabilized, the product was analyzed by gas chromatography to obtain the conversion rate of carbon monoxide and the selectivity of aromatics when C$_{1-4}$ gas-phase hydrocarbons Catalyst Regeneration Performance Test Example 25

The deactivated catalyst in Example 19 was treated with a mixture of 2% oxygen and 98% nitrogen by volume at 550° C. for 10 h to regenerate the catalyst for one round and react under the conditions of Example 19. It was regenerated for five rounds in the same way, and the catalytic activity data after 500 h of each round of reaction was selected for comparison. The results were shown in Table 3.

TABLE 3

Catalytic reaction results in Example 25

| Number of Regeneration | Conversion Rate of Carbon Monoxide (%) | Selectivity of Aromatics When C$_{1-4}$ Gas-phase Hydrocarbons were not Recycled (%) | Selectivity of Aromatics When C$_{1-4}$ Gas-phase Hydrocarbons were Recycled (%) | Life of Each Round (h) |
|---|---|---|---|---|
| 1 | 20.3 | 54.3 | 96.1 | 3500 |
| 2 | 21.0 | 53.9 | 95.3 | 3700 |
| 3 | 21.5 | 55.6 | 96.7 | 3400 |
| 4 | 21.1 | 55.0 | 96.0 | 3500 |
| 5 | 20.7 | 52.3 | 94.5 | 3600 |

The above are only a few examples of the present application, and are not intended to limit the present application in any way. Although the present application is disclosed in the above with preferred example, it is not intended to limit the present application. Any one skilled in the art can understand that other changes and modifications by using the above technical content without departing from the scope of the technical solution of the present application are equivalent to equivalent embodiments and belong to the scope of the technical solution.

The invention claimed is:

1. A method for preparing aromatics from syngas, comprising:
   a) contacting a raw material stream containing syngas with a catalyst in a reaction zone under reaction conditions sufficient to convert at least part of the raw material to obtain a reaction effluent;
   b) separating the reaction effluent to obtain at least a recycle stream containing gas-phase hydrocarbons having 1 to 4 carbon atoms and unconverted syngas and a liquid stream containing hydrocarbons having 5 or more carbon atoms;
   c) returning the recycle stream to the reaction zone; and
   d) separating aromatic products from the liquid stream,
   wherein the catalyst comprises at least one of an inert carrier-confined highly dispersed metal oxide material, an acidic molecular sieve, and a graphite powder and a dispersant, wherein in the inert carrier-confined highly dispersed metal oxide material, the inert carrier is at least one of silicon oxide and aluminum oxide, and the content of the metal oxide in terms of metal is less than or equal to 10% by mass, based on the weight of the inert carrier-confined highly dispersed metal oxide material; and the acidic molecular sieve is selected from modified acidic ZSM-5 molecular sieve, modified acidic ZSM-11 molecular sieve and mixtures thereof.

2. The method of claim 1, wherein
   the reaction zone comprises a fixed bed reactor, or a plurality of fixed bed reactors in series and/or parallel;
   the reaction conditions comprise: a reaction temperature of ranging from 300° C. to 450° C., a reaction pressure of ranging from 0.5 MPa to 10.0 MPa, a molar ratio of hydrogen to carbon monoxide in the syngas of ranging from 1:9 to 9:1, and the volume hourly space velocity of syngas under the standard state of ranging from 1000 $h^{-1}$ to 20000 $h^{-1}$;
   the aromatics are at least one selected from monocyclic aromatics having 6 to 11 carbon atoms;
   the gas-phase hydrocarbons having 1 to 4 carbon atoms are at least one selected from methane, ethane, ethylene, propane, cyclopropane, propylene, n-butane, isobutane, cyclobutane, 1-butene, 2-butene, isobutene and butadiene;
   the metal oxide is an oxide of at least one of zinc, chromium, zirconium, copper, manganese, platinum and palladium;
   the content of the metal oxide in the inert carrier-confined highly dispersed metal oxide material in terms of metal is less than or equal to 5% by weight, based on the weight of the inert carrier-confined highly dispersed metal oxide material;
   the particle size of the metal oxide in the inert carrier-confined highly dispersed metal oxide material is less than or equal to 100 nm;
   the modification of the acidic molecular sieve is one or more of phosphorus modification, boron modification, silicon modification, alkaline earth metal modification and rare earth metal modification;
   the atomic ratio of silicon to aluminum in the acidic ZSM-5 and ZSM-11 molecular sieves is Si/Al=3 to 200; and
   the shape of the catalyst is spherical, bar-shaped, cylindrical, semi-cylindrical, prismatic, clover-shaped, ring-shaped, pellet-shaped, regular or irregular particle-shaped or plate-shaped.

3. The method of claim 1, wherein the catalyst comprises a range from 10% to 90% by weight of the inert carrier-confined highly dispersed metal oxide material, a range from 10% to 90% by weight of the acidic molecular sieve, ranging from 0% to 10% by weight of the graphite powder, and a range from 0% to 40% by weight of the dispersant; wherein the total content of the inert carrier-confined highly dispersed metal oxide material and the acidic molecular sieve is in a range from 60% to 100% by weight, and the weight percentage is based on the total weight of the catalyst.

4. The method of claim 1, wherein the catalyst comprises a range from 20% to 80% by weight of the inert carrier-confined highly dispersed metal oxide material, a range from 20% to 80% by weight of the acidic molecular sieve, ranging from 0% to 5% by weight of the graphite powder, and a range from 0% to 30% by weight of the dispersant, the weight percentage is based on the total weight of the catalyst.

5. The method of claim 1, wherein the average particle size of the inert carrier-confined highly dispersed metal oxide material is less than or equal to 5 mm, and the average particle size of the acidic molecular sieve is less than or equal to 5 mm.

6. The method of claim 1, further comprising preparing the catalyst by the following steps:
   (1) providing an inert carrier-confined highly dispersed metal oxide material;
   (2) providing a modified acidic molecular sieve; and
   (3) mixing at least one of the inert carrier-confined highly dispersed metal oxide material obtained in step (1), the modified acidic molecular sieve obtained in step (2) and optional graphite powder and dispersant, and molding the resulting mixture.

7. The method of claim 6, wherein the method for preparing the catalyst further comprises at least one of:
   in step (1), the inert carrier-confined highly dispersed metal oxide material is prepared by a precipitation-calcination method, or the inert carrier-confined highly dispersed metal oxide material is prepared by a sol-gel method;
   the modified acidic molecules are selected from ZSM-5 molecular sieve and ZSM-11 molecular sieve modified with phosphorus, boron, silicon, alkaline earth and/or rare earth metals; and
   in step (3), the mixture is molded into catalyst particles using an extrusion method or a molding method.

8. The method of claim 6, wherein in step (1) of the method for preparing the catalyst, the inert carrier-confined highly dispersed metal oxide material is provided by a method comprising the steps of: formulating a salt of catalyzing active metal and an aluminum salt into an aqueous solution of mixed metal salt; contacting the aqueous solution of mixed metal salt with an aqueous solution of precipitant to coprecipitate the metal ions in the aqueous solution of mixed metal salt; aging; and washing, drying, and calcining the precipitate to prepare the inert carrier-confined highly dispersed metal oxide material.

9. The method of claim 8, further comprising at least one of:
- the salt of catalyzing active metal and the aluminum salt are selected from hydrochloride, sulfate and nitrate;
- the precipitant is selected from sodium carbonate, potassium carbonate, ammonium carbonate, sodium bicarbonate, potassium bicarbonate, ammonium bicarbonate, ammonia water, sodium hydroxide, potassium hydroxide and mixtures thereof;
- the coprecipitation is performed at ranging from 0° C. to 90° C.;
- the pH value during the coprecipitation is in a range from 7.0 to 8.5;
- the aging time is not less than 1 h; and
- the calcination is performed at ranging from 300° C. to 700° C.

10. The method of claim 6, wherein in step (1) of the method for preparing the catalyst, the inert carrier-confined highly dispersed metal oxide material is provided by a method comprising the steps of: adding an aqueous solution of a salt of catalyzing active metal and an aqueous solution of a precipitant to the siloxy group compound, allowing the coprecipitation and sol-gel reaction to proceed, and then washing, drying and calcining the obtained gel to prepare the inert carrier-confined highly dispersed metal oxide material.

11. The method of claim 10, further comprising at least one of:
- the precipitant is selected from ammonium carbonate, ammonia water, ammonium bicarbonate, ammonium dihydrogen carbonate, urea and mixtures thereof;
- the siloxy group compound is an alkyl orthosilicate, selected from methyl orthosilicate, ethyl orthosilicate, n-propyl orthosilicate, isopropyl orthosilicate, n-butyl orthosilicate, isobutyl orthosilicate, t-butyl orthosilicate and mixtures thereof.

12. The method of claim 1, wherein the reaction conditions comprise: a reaction temperature of ranging from 320° C. to 400° C., a reaction pressure of ranging from 5.0 MPa to 10.0 MPa, a molar ratio of hydrogen to carbon monoxide in the syngas of ranging from 1:9 to 1:1, and the volume space velocity of syngas under the standard state of ranging from 1000 $h^{-1}$ to 5000 $h^{-1}$.

* * * * *